United States Patent [19]

Carter

[11] Patent Number: 4,498,485
[45] Date of Patent: Feb. 12, 1985

[54] INTERFERON AND INTERFERON INDUCERS COMBINED WITH TOBACCO PRODUCTS

[75] Inventor: William A. Carter, Birchrunville, Pa.

[73] Assignee: Hem-Sub, Inc., Philadelphia, Pa.

[21] Appl. No.: 386,447

[22] Filed: Aug. 5, 1982

[51] Int. Cl.³ .................... A24B 15/20; A24B 15/30
[52] U.S. Cl. .................................. 131/331; 131/334; 131/335; 131/343; 131/310; 131/352
[58] Field of Search ............... 131/309, 310, 331, 332, 131/334, 335, 343, 337, 352

[56] References Cited

U.S. PATENT DOCUMENTS 3,339,558  9/1967  Waterbury .
3,667,478  6/1972  Waterbury .

FOREIGN PATENT DOCUMENTS 3064  7/1979  European Pat. Off. ............ 131/337

OTHER PUBLICATIONS

Alien Property Custodian to Lande: Title "Tobacco Products and Process of Making the Same." Published Mar. 1939; S.N. 201,010.

Primary Examiner—V. Millin
Attorney, Agent, or Firm—Cushman, Darby & Cushman

[57] ABSTRACT

Methods and compositions are provided for preparing stabilized interferons and for combining stabilized interferon with cigarettes. Special domains of the interferon molecule are recognized by methods which are described. A means for constructing these domains by recombinant DNA technology is detailed. A method for stabilizing natural interferons is also described. A process for combining the stabilized interferon with cigarettes is presented.

The combination of interferons and cigarettes is synergistic, especially because interferon effects are magnified at elevated temperatures and because interferon has a preferential effect on tumor cells, but for other reasons as well. The process is not obvious and will be beneficial to a large segment of mankind; those who use tobacco products.

32 Claims, 1 Drawing Figure

INTERFERON AND INTERFERON INDUCERS COMBINED WITH TOBACCO PRODUCTS

Several patents attempt to medicate cigarettes generally (U.S. Pat. No. 977,635 by A. B. Klein; U.S. Pat. No. 1,974,242 by J. L. Jordan, Jr. et al.; U.S. Pat. No. 2,418,296 by S. S. Frederickson; U.S. Pat. No. 4,021,364 by P. Speiser et al.) with vitamins (U.S. Pat. No. 2,198,188 by A. Viscardi; U.S. Pat. No. 2,890,973 by G. Fachini; U.S. Pat. No. 3,244,180 by B. Stone, U.S. Pat. No. 3,339,558 by N. J. Waterbury; U.S. Pat. No. 3,667,478 by N. J. Waterbury) with electric charges (U.S. Pat. 3,240,212 by R. Roysten), etc. These medications are claimed to be beneficial on their own or to neutralize or reduce toxic effects of smoke inspired by smokers, effects such as growth depression, bad breath, hay fever, cancer, emphysema and heart disease. These patents presumably provide means for restoring reserves of biological compounds which are depleted by cigarette smoke or for counteracting the alleged bad effects of cigarette smoke, but they do not claim to provide more effective medication than is supplied by the separate administration of the medicinal. Now in considering these results obtainable heretofore I conceived that significantly better results could be reached by using a medicinal which will act synergistically with cigarette smoking. My invention provides the synergy by combining cigarettes with a natural medicinal, interferon, whose activity is enhanced by the conditions of smoking and which is targeted to perturbed cells by the smoke. My invention further provides novel processes for stabilizing interferon so that its biological activity can be retained during the usual conditions of cigarette manufacture; storage and use.

Interferon was first characterized as a potent antiviral agent (Isaacs and Lindenmann, Proceedings Royal Society London, Series B. Volume 147 pp. 258-276, 1957) and since has been found to have antigrowth (anticancer) activities (Paucker et. al., Virology, Volume 17 pp. 324-334, 1962) (reviewed by Taylor-Papadimitriou, in Interferon edited by Gresser, Volume 2, pp. 13-46, 1981). Interferon also activates the tumor immune system (Trinachieri et. al., Journal of Experimental Medicine, Volume 147 pp. 1299-1305, 1978). I first deduced that interferon at appropriate concentrations can actually convert certain malignant cells to normal cells through a process termed "differentiation" or cell maturation (Carter et. al., grant application document P01CA29545 proposed July, 1980; Gillespie and Carter, Texas Reports in Biology and Medicine, 37-42, 1982). Experimental evidence cited in Gillespie and Carter, ibid) supports my deductions that interferon can eliminate cancer in its early stages if the tumor cells are exposed to th interferon over time such that the tumor cells are redirected to become normal through a maturation or normal development process. This discovery indeed implies that tumor cells will be eliminated *as they emerge* in the human body if an efficient method is devised whereby the interferon is placed repeatedly and efficiently at the bodily sites from which emerge the first small nests of malignant cells. Such tumor nests if left unchecked, usually spread beyond their local boundaries eventually leading to symptomatic illness and death. Further, I have obtained evidence that individuals afflicted with lung cancer have a defect in their immune surveillance systems which apparently results in part or whole from inadequate elaboration of interferons within their bodily systems (Strayer, Carter, et. al., in press, Cancer Research, Vol. 44, pages 370-374, 1984).

This invention consequently relates to the stabilization of interferon for the purpose of combining interferon with products whose adverse effects interferon might prevent but whose manufacture, storage or use is incompatible with the preservation of interferon's biological activity. The two processes I describe for stabilization of interferon are novel and are not obvious.

As an important example, this invention relates to the stabilization of interferon protein for the purpose of combining interferon with smoking devices, collectively termed 'cigarettes'. Such a combination is synergistic. It is synergistic because the effect of interferon is heightened in those cells which are warmed by the cigarette smoke, e.g., the *hypothermic effect* discovered by Heron and Berg (Nature 274: 508-510, 1978). In this work it was shown that an environmental temperature elevation as small as 2°-3° C. can serve to augment the effect of low doses of interferon in inhibiting the growth of lymphoma cells some 800%. Even more recently, Delbruck et. al., (Biomedicine 33: 239-241, 1980) demonstrated a 100-fold potentiation of the ability of interferon to kill osteosarcoma cells by increasing the temperature only 2°, from 37° to 39° C. Since the exit smoke from a cigarette is 40°-50° C. (Report of the Surgeon General, Department of Health, Education and Welfare, 1979 page 14-36) the surface of cells of the oral cavity, throat and possibly the lung airways will be materially elevated and will potentiate the effect of interferon carried to these cells. Also, it is synergistic because the hydrophobic stabilized interferon combines with smoke constituents, for example by hydrophobic carcinogens like 3,4 benzopyrene and particles carrying this carginogen, and the interferon, consequently becomes *targeted specifically* to cells perturbed by smoke carcinogens, potential cancer cells. Moreover, as demonstrated by Horoszewics et. al., (Science 206:1091-1093, 1979) it is synergistic because interferon interacts *preferentially* with tumor cells, e.g., those caused by previous smoking. Finally, the synergy is heightened because interferon is administered *simultaneously and locally* with the cigarette smoke. It can be noted that the amount of interferon taken in by the smoker is in direct relation to the number of cigarettes smoked, i.e., to the exposure to carcinogenic substances. Also, the smoker cannot fail to remember to take this interferon supplementation before smoking since the interferon is a constituent part of the smoking device. Therefore, though it may be apparent that interferon is a potential cure for cancer caused by cigarette smoking whether administered sequentially or simultaneously, the synergy I have discovered between interferon and cigarettes is not apparent and suitable means for stabilizing interferon for combination with cigarettes is not obvious.

Airborne environmental pollutants, including cigarette smoke, may increase the chance of lung cancer and possibly other cancers, but the latent period is long and hitherto it has been impossible to arrest or eradicate efficiently the resultant cancer at an early stage. Many human cancers seem to be the consequence of an individual with a bodily predisposition (whether inherited or acquired) to this disease being repeatedly exposed to a second event termed the environmental trigger (see review in U.S. Department of Research, 1971-1981, 1981). The invention includes a method whereby both of the above conditions associated with the development of lung cancer are corrected, namely: (1) externally prepared interferon is provided to the bodily tissues as a *replacement* for any possible defects (whether hereditary or acquired) in its manufacture by the body itself (thereby restoring the bodily immune defenses against cancer), and further (2) the cancer promoting effects of noxious carcinogenic substances, which may in any case override the bodily defense system, are attacked and ultimately eliminated by the additional *locally targeted* effects of the deposited interferon, namely through its added ability to directly convert the malignant cell to normal through a 37 differentiation" process.

The objective of the invention is to take advantage of the regular practice of cigarette smoking to facilitate transfer to *specific parts of the body* of this natural bodily substance with many useful effects.

The introduction of interferon into tobacco products thus provides a novel means of transporting interferon efficiently to affected cavity, lungs and nasal spaces, thereby producing locally the various interferon effects, including the various defenses provided by interferon which collectively should eliminate the cancer cells as they emerge following a period of prolonged exposure to a variety of airborne environmental pollutants including possible carcinogenic substances. As a result, the invention should decrease the incidence of various cancers, especially those occurring in the lungs, throat and oral cavity. The invention has also been tested with reference to increasing the body's overall resistance to other diseases such as those resulting from the chronic inhalation of foreign particulate matter (associated with development of emphysema and chronic bronchitis) and inhalation of airborne contagious human viruses (associated with diverse infectious disease such as pneumonia, flu syndrome, colds, etc.). Results of these in vitro tests (see Examples) indicate that an individual's *regular practice of the inventin* (that is, smoking cigarette products impregnated with different types of interferon) should result in a *multiplicity of beneficial bodily effects* including reduced rates of cancer, reduced rates of emphysema/chronic bronchitis as well as general better health through a concomitant reduction in viral and infectious illnesses. A decreased susceptibility to certain types of vascular (blood vessel) disease, thought to be increased in heavy smokers, may also occur as the interferon is known to antagonize certain factors which contribute to the closing (occlusion) of blood vessel walls.

To accomplish this multiplicity of beneficial effects, a process is provided for combining all types of interferons and all types of interferon inducers (substances which trigger interferon production in the body) with cigarettes. This process will clearly be beneficial to mankind by reducing the incidence of cancer and other dread diseases whose harmful effects can be neutralized by interferon placed repeatedly in physical juxtaposition with the vulnerable and/or early diseased cells. The process may also be adapted to a whole range of other carcinogenic substances whose harmful effects are counteracted by the localized effect of high concentrations of interferon at their portals of entry to the human body.

However, human interferons in nature are a group of proteins and the biological activity of proteins are often labile (destroyed) under certain conditions (for example, thermal changes, changes in acid/alkalinity environment, turbulence, and/or shearing effects {vortical rotation}, etc.). To reduce lability of the biological activity of interferons, we have further introduced a new class of interferons which is the preparation of pieces (components or special amino acid sequences) of either natural or synthetic interferons to provice the molecular stability in maintaining the desired biological effects under a broad range of different environmental conditions. The fragments or pieces can typically be approximately 10 to 15% of the normal molecular length of interferons, being more or less 25-45 amino acids in length rather than the usual approximately 162 component amino acids. The determination of these essential amino acid pieces (or sequences) from the entire length of human interferons was made possible by our novel analysis (facilitated by computer) of domains (or regions) of many different interferons conserved during vertebrate *evolution*. In addition to desirable physico-chemical properties, the interferon pieces or sequences will also be useful from a cost/effectiveness wiewpoint in that their small size will allow their large scale production at a fraction of the cost of the whole interferon molecules, and by a variety of manufacturing modes, such as recombinant DNA methodology, solid phase synthesis, etc.

However, I recognize that the production and testing of stable, bioactive pieces of interferon may impose unsatisfactory delays in implementing this invention. Accordingly, I invented a simple and economical means for stabilizing natural interferon by limiting the number of alternate states the molecule can assume. I accomplished this by forming weak hydrophobic interactions between interferon and another substance, usually a protein.

I combine interferon with tobacco products, including cigarettes. I describe necessary and novel means of stabilizing interferons by using "pieces of interferon" and by combining interferon with certain carriers—to retain biological activity in the face of high temperatures, destructive chemicals and prolonged storage. Some of the stabilized interferon combines with smoke particles and is thereby targeted to perturbed cells, providing a *synergistic action* between interferon and cigarette smoke not possible by introducing interferon separately, e.g., with an atomizer.

BRIEF DESCRIPTION OF THE PRIOR ART

Carter W. A., 1979, Life Sciences 25: 717-728; Gillespie and Carter, 1982 a, *Handbook of Experimental Pharmacology of Interferon*, pages 45-63, Derynk et. al., 1980, Nature 285: 542-547; Gillespie and Carter, 1982, Texas Rep. Biol. Med., pages 37-42; Carter, W. A., *Handbook of Experimental Pharmacology on Interferon*, 1984, 1982; Strayer, D. R., Carter, W. A., et. al., 1982, Abstracts of 13th International Cancer Congress; Carter, W. A. et al., 1980. Program Grant Proposal P01CA29545 to the National Cancer Institute; Carter, W. A. and Horoszewicz, J. S. 1980, Pharmacology and Therapeutics 8: 359-377; Isaacs and Lindenmann, Proceedings Royal Society London, Series B Volume 147 pp. 258-267 (1957); Paucker et. al., Virology Volume 17 pp. 324-334 (1962); Taylor Papadimitriou, in "Interferon" (Gresser, ed.,), Volume 2 pp. 13-46 (1981); Derynk et. al., Nature, Volume 285 pp. 542-547 (1980); Goeddel et. al., Nature, Volume 290 pp. 20-26 (1980); Shepard et. al., Nature, Volume 294 pp. 563-565 (1981).

SUMMARY OF THE INVENTION

Methods and compositions are provided for creating and purifying pieces of interferon with biological activity and with enhanced stability. Methods and compositions are also provided to combine pieces of interferon or whole interferon (or interferon inducers) with cigarettes in such a way as to permit delivery of enhanced interferon activity to cells exposed to cigarette smoke. A number of desirable and beneficial results will accrue, including:

(1) Interferon and cigarette smoking act *synergistically* to provide surveillance against emerging cancer cells, infecting respiratory viruses, etc. The biological effects of interferon in creating these desired medicinal effects is heightened by increased temperatures in tobacco smoke (the hyperthermic effect discovered by Heron and Berg, Nature 274: 508-510, 1978).

(2) Any carcinogenic effect of cigarette smokers can be overcome at its point of entry into the various human tissues, since the interferon, being *co-transported* with the putative noxious agents (either volatile matter or particulate matter) to the target human cells, stimulates the cells to become normal rather than continue on their malignant course.

(3) Any bronchial destructive effect of foreign particulate matter (elemental carbon particles, etc.) will be minimized or eliminated altogether by the demonstrated ability of the invention to increase the effectiveness of cells (macrophages) which normally serve the lungs by scavenging, engulfing, and otherwise destroying noxious foreign particular matter within the lung microenvironment, thus preventing formation of such debilitation and pathologic diseases as chronic bronchitis, emphysema, etc.

(4) Any localized immunological defects in the lung attributable to low interferon levels are immediately corrected by the invention and further it is reasonably believed that the immune cells (comprising part of the body's whole immune system) augmented in their abilities following passage through the lung and transient exposure to the deposited interferon, may then circulate to other parts of the body. In this way, the interferon although applied locally, may have beneficial effects multiplied and ultimately distributed to various other parts of the body (referred to as a systemic effect). Such benefits could involve other desirable systemic effects, such as the inactivation of platelet growth factor, a component in the overall process which occludes arteries and veins by a pathologic process.

(5) Any exposure to viral agents throughout the entire human respiratory tree (nose, mouth, pharynx, trachea, lungs, etc.) will be met with greatly heightened tissue resistance because of the antiviral effects of the interferon molecules distributed throughout various bodily areas. Whenever the invention is regularly practiced, the interferon on respiratory tissues which has lost its biological activity is regularly replaced with fresh, active interferon molecules.

We combine interferon with tobacco products, including cigarettes. We describe necessary and novel means of stabilizing interferons by using "pieces of interferon" and by combining interferon with certain carriers—to retain biological activity in the face of high temperatures, destructive chemicals and prolonged storage. Some of the stabilized interferon combines with smoke particles and is thereby targeted to perturbed cells, providing a *synergistic action* between interferon and cigarette smoke not possible by introducing interferon separately, e.g., with an atomizer.

BRIEF DESCRIPTION OF THE FIGURE

FIGURE 1 is a schematic illustration showing how interferon may be added to cigarettes.

DESCRIPTION OF THE SPECIFIC EMBODIMENTS

This invention employs the novel practice of eliminating or modifying a part of the interferon molecule to create enhanced stability while preserving biological activity. The process of this invention produces a synergistic combination by combining interferon with cigarettes to provide continual molecular surveillance and elimination of emerging cancer cells in tissues affected by cigarette smoke. "Cigarettes" will be taken to include cigars, pipes, etc. i.e., all smoking devices. The term "interferon" and "pieces of interferon" will be used interchangeably to include the natural interferon molecules as well as all variants with modifications of polypeptide and carbohydrate moieties, such as may be produced not only in human cells, but in non-human cells including bacteria, yeast, monkey cells, etc. Furthermore, this invention describes a means for stabilizing natural interferon and its derivatives by limiting the number of alternate states these molecules can assume, e.g., by attaching said interferon or derivatives to a hydrophobic carrier.

The process of this invention will be divided into the following stages:

I. Recognition of Interferon Domains

II. Preparation of Pieces of Interferon with Select Domains

III. Stabilization of Interferon with Carriers

IV. Combination of Pieces of Interferon and Whole Interferon Molecules with Cigarettes V. Combination of Interferon Inducer/Activators with Cigarettes

I. Recognition of Interferon Domains

Genes which code for interferon have been cloned (e.g., Derynk, et. al., Nature, Volume 285 pp. 542-547, 1980). These genes have been sequenced Goeddel et. al., Nature, Volume 290 pp. 20-26, 1980; Derynk, et. al., Nature, Volume 285 pp. 542-547, 1980) and the primary structure of nine of the various interferons determined. Using computer programs we have deduced domains necessary for certain biological properties (Gillespie and Carter, Handbook of Experimental Pharmacology of Interferon, 1984, of the interferon system and prepared the substances for immobilization in cigarettes.

The interferon which is essential but not necessarily sufficient for eliciting biological responses in cells, including the antiviral and anticancer responses is conferred by amino acids 25-40 and 115-141. Since all interferons elicit both antiviral and antineoplastic responses, the position of this domain is deduced on the basis of the conservation of the primary amino acid sequence of this domain from one species of interferon to another, especially when said conservation is unexplained by conversation of mRNA (messenger RNA) or protein shape. The biological response domain may be exposed to the external environment Gillespie and Carter, 1982), thus facilitating interaction with other cellular constituents. Streuli et. al., (Proceedings National Academny of Science, U.S.A., Volume 78 pp. 2848-2852, 1981) proposed that both ends of the interferon molecule were required to elicit biological activity in a spectrum of host cells.

The interferon domain deduced to be essential but not necessarily sufficient for binding to specific cell receptors is amino acids 115–141 (Gillespie and Carter, 1982). The position of this demain is deduced from homology with a region of the B subunit of cholera toxin, (Lai, Journal Biol. Chem. Volume 252 pp. 7249–7256, 1977) a substance which competes with interferon for binding to cell receptors.

At least two pieces of interferon will be useful for providing biological surveillance to cigarettes. One piece consists of the biological response domain itself, either pure or linked to another moiety of facilitate entry into susceptible cells. A second piece consists of the biological response domain contiguous with the receptor binding domain. Other pieces of interferon, including the entire polypeptide and prosthetic groups and additions thereto or deletions therein or both, or modifications thereof, may also be useful.

Additionally, the invention may be practiced with any of the naturally occurring or synthetic (bacterial or yeast) produced whole interferon molecules referred to commonly as alpha (leukocyte-type), beta (fibroblast type) or gamma (immune type) interferons. Advantages of the interferon pieces include: stability, ease of displacement from cigarette to lungs (because of lower molecular weight), possibly better tissue penetration and low antigenicity.

II. Preparation of Pieces of Interferon with Select Domains

Pieces of interferon can be prepared in several ways. By way of illustration, one suitable process is described. Other means, such as chemical modification of natural interferon or chemical modification of cloned (synthetic) entire interferon, interferon induces, etc., are also readily apparent and are obvious extensions of the discovery itself.

Cloned interferon genes can be cut in specific places with specific restriction endonucleases. The resulting interferon gene fragment, coding for a piece of the interferon polypeptide can be fused with an expression vector containing RNA polymerase promotor, ribosome binding site, initiation codon and whatever other signals may be necessary. This recombinant DNA can be introduced into suitable host cells for the purpose of snythesis of the piece of interferon.

Specifically, 5μg of the gene for human interferon Beta when "tailed" with polyA.dT and cloned in pBR322 was incubated at 37° for 2 hours with 50 units of EndoR.Pst 1 in 20 mM tris, pH 7.4 10 mM $MgCl_2$, 50 mM $(NH_4)$ $SO_4$ and 100 mg/ml of bovine serum albumin to cleave the interferon gene, leaving a single-stranded end from bases 203–206. The DNA was made 0.3M in potassium acetate and precipitated from ethanol. The DNA was dissolved in 100 ml of 50 mM potassium phosphate, pH 7.4, 6.7 mM $MgCl_2$, 1 mM mercaptoethanol, 35 mM deoxyademosine and deoxycytidine, and 25 units of the Klenow fragment end of *Escherichia coli* DNA polymerase. The DNA was made 0.3 mM in potassium acetate and precipitated from ethanol. The precipitate was dissolved in 100 ml of 30 mM sodium acetate, pH 4.6, 50 mM NaCl, 1 mM $ZnSO_4$, 5% glycerol and 25 units of S1 nuclease and incubated at 37° for 1 hour. This produced an interferon gene fragment with a blunt end complete up to nucleotide 204, the first based in codeward for leucine at position 45 . Sodium acetate was added to 0.3 M and the DNA precipitated from ethanol.

Separately, 5 μg of the gene for human interferon Beta (tailed" with polydA.dT and cloned in pBR322 was incubated at 37° for 2 hours with 50 units of Endo R MboII in 10 mM tris, pH 7.9, 6 mM KCL, 10 mM $MgCl_2$, 1 mM dithiothreitol and 100 mg/ml of bovine serulm albumin. The DNA was precipitated from ethanol and treated with S1 nuclease as described above. The 288 base pair, blunt end fragment containing nucleotides 401–688 of the interferon gene was purified by electrophoresis through 3% agarose. An aliquot of 0.25 mg of this fragment was incorporated with 5 μg of Pst 1—treated, DNA polymerase—treated and S1 nuclease—treated DNA.

The precipitated consisting of two DNA fragments was dissolved in 10 ml of 10 mM tris pH 8.0 containing 10 units of bacterial alkaline phosphate and incubated at 37° for 2 hours. The solution was then diluted to 100 ml with 2.3 M sodium acetate, held at 65° for 30 minutes extracted once with $CHCL_3$, then precipitated from ethanol. The precipitate was dissolved in 10 ml of 70 mM tris, pH 7.5, 100 mM KCl, 10 mM $MgCl_2$, 5mM dithiothreitol, 300 mM riboadenosine triphosphate and 1 unit of polynucleotide kinase and 10 units T4 DNA ligase and incubated at 37° for 2 hours.

The recombinant DNA so formed contained an interferon gene lacking nucleotides 205–400 which will code for an interferon polypeptide lacking amino acids 46–111.

In examples which follows, this material shall be referred to as "interferon fragment polypeptide."

This recombinant interferon fragment can be inserted into many suitable vectors for expression in bacterial or mammalian cells using conventional techniques. Interferon or pieces of interferon can be purified by standard methodology although the invention can be practiced with interferons less than 1% pure, provided no otherwise harmful substances are present. For example proteins in solutions containing interferon are bound in Cibachrom blue sepharose in the absence of ethylene or propylene glycol. The column is washed with a variety of solutions which remove most proteins, except interferon and the interferon is eluted with solutions containing ethylene or propylene glycol or other suitable eluting agents (Carter et. al., Pharmacology and Therapeutics, Volume 8 pp. 359–377, 1980). If desired, further purification of Cibachrom blue fractions or other material can be achieved by passing interferon-containing solutions over column matrices containing anti-interferon antibodies, using conventional conditions for binding and elution.

The recombinant DNA described above can be prepared using some of all of the same enzymes under different conditions or in different sequences or using variants of the above stated enzymes or interferon genes. Other suitable recombinant DNAs can be formed using other enzymes and other protocols. Finally, the use of recombinant DNA to obtain pieces of interferon is merely illustrative of a means of generating a piece of interferon. Other means, such as solid state synthesis, proteolytic cleavage of intact material or genetically cloned interferon prepared in bacteria and yeast can be equivalently used.

III. Stabilization of Interferon with Carriers

Interferon, like other proteins, is a relatively labile chemical. It depends on a very specific three-dimensional orientation of its various linearly-arrayed amino acids for solubility in aqueous solutions and for biological activity. Specifically, domains of the interferon molecule responsible for binding to cells for eliciting complex biological response must be properly exposed and aligned. However, a vast array of alternate non-functional orientations are also possible and can freely form. These alternate states are encouraged by heat, certain external chemicals and prolonged storage.

One solution toward preventing the formation of inactive alternate states is to build interferon molecules with a limited number of alternate states, i.e., the pieces of interferon described in Part II. Another solution, developed by the inventor is to restrict the formation of alternate states by immobilizing the interferon on a carrier molecule or structure.

Active enzymes are often found as part of complex structures, being attached to cell membranes, nucleic acids, proteins, etc., and the enzymes are usually more stable in the complexed state. To evaluate the feasibility of such an approach we constructed several column matrices containing various ligands which might be effective stabilizers (see Carter, W. A., and Horoszewicz, J. S., 1980, Pharmac. Ther. 8:359-377). We characterized the column with albumin attached to it. We took an undialyzed interferon preparation, 100 ml, containing 11,500 units and 0.99 mg protein per ml and applied it to a column by means of a peristaltic pump at a flow rate of 60 ml per $cm^2$ per hour. The albumin column was equilibrated with a 0.02 M sodium phosphate (pH 7.4) containing 0.15 M NaCl. The eluent from the column was divided by a stream-splitting device in a ratio of 1:9. The 10 percent portion of the eluent was collected into 1 ml of a 1 percent solution of bovine serum albumin, containing 0.02 M sodium phosphate and 0.15 M, NaCl, and used to assay interferon activity. The 90 percent portion of the eluent was used to mesure the protein concentration. The breakthrough fractions contained about 98 percent of the applied protein and less than 1 percent of the applied interferon activity. Further elution of the column was done with 50 percent (v/v) ethylene glycol and 50 percent 0.04 M phosphate, (pH 7.4) and 0.30 M NaCl. The remainder (86 percent) of the interferon activity was recovered with very little (less than 2 percent) of the original protein. Some of these experiments were recently published (Carter, W. A., 1982, Methods in Enzymology 78:576-582, 1981).

The above experiment showed that interferon could be coupled with serum albumin while most other cellular proteins could not be. Experiments with other immobilized proteins such as cytochrome C showed that interferon has a general property of combining with proteins. We had hypothesized that the strong hydrophobic nature of interferon forces interactions with ordinarily sequestered hydrophobic pockets of other proteins and this experiment suggested the accuracy of the hypothesis. Whatever the mechanism, the above experiment encouraged the development of complexes with proteins to stabilize interferon.

The prodecure we developed and desired to patent for this purpose is as follows: Human interferon can be prepared by any conventional means from any biological source —from human cells, from recombinant micro-organisms, etc. After purification, human serum albumin or other proteinacious carrier can be added in excess, usually to 3 mg/ml. The solution can be dialyzed against phosphate buffered-saline or another appropriate buffer, then the material can be freeze-dried. In a typical example 1 million units of purified interferon was freeze-dried with 3.46 mg sodium phosphate. The stability of such a preparation is documented in Example 5.

Various alternations of this procedure are acceptable in this rapidly changing field. Other carrier proteins than albumin or cytochrome C are acceptable. Other carrier molecules or structures may also be acceptable, such as lipids, small hydrophobic ligands, membrane fragments, or even solid particles. Other means of attachment, such as ionic or covalent bonds may be suitable as long as the result is to stabilize the interferon activity while still permitting its combination with cigarettes. Other salts or buffers or other concentrations of salt or buffer (including no salt or buffer) may be acceptable; we have not explored variants in these parameters. In some instances dialysis may be unnecessary. Basically, the object of this process is to provide a stable form of interferon which may be combined with cigarettes and which will retain biological potency.

IV. Combination of Pieces of Interferon with Cigarettes

In the following section "interferon" represents whole interferon and "pieces of interferon" as defined earlier and, conversely, the term "pieces of interferon" as used in this section is taken to include whole molecules.

Interferons of all known human types were prepared in the inventor's laboratories by standardly accepted techniques, (see for natural fibroblast {beta} interferon, Carter and Horoszewicz, Pharmacology and Therapeutics, Volume 8 pp. 359–377, 1980; for natural leukocyte {alpha} interferon, Mogensen and Cantell, Pharmacology and Therapeutics, Volume I pp. 369–381, 1977; for natural immune {gamma} interferon, Mizarhi, O'Malley, Carter, et. al., Journal of Biological Chemistry, Volume 253, pages 7612–7615, 1978).

Interferon molecules must be added to cigarettes in a manner which preserves interferon's biological activity and permits transmission of interferon through the oral cavity and into the lungs by inhaled cigarette smoke. The details of the combination process must maximize the chance of desirable biological activity, e.g., anti-tumor, immunological, and antiviral effects, in the lips, oral cavity, and lungs.

Several procedures for combining pieces of interferon with cigarettes fulfill these criteria. One typical example is given below but in no way can it be considered to be the only suitable form of the process.

Figure 1:
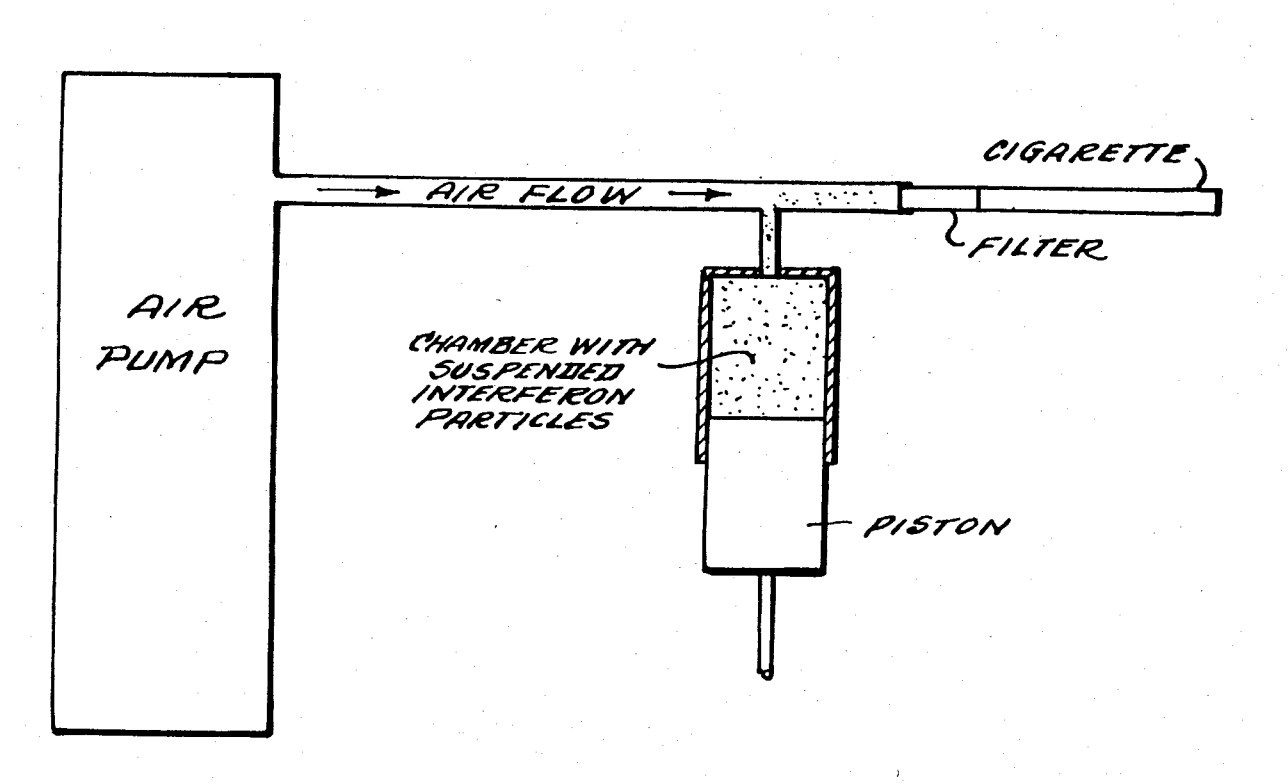

Pieces of interferon and entire molecules have been prepared as exemplified in Section II and III of this application or otherwise and lyophilized to a fine, dry powder, using conventional procedures and equipment. Interferon of 0.01–100% purity is suitable. Commonly, a mixture of 1 part interferon and 99 parts of human albumin, fraction V, have been lyophilized together to yield particles of desired bulk and consistency without undesirable biological effects. Other mixtures are possible and are considered equivalent, including the combination of interferon with carriers like particles of cellulose and common salts, etc., as long as the features mentioned above (consistency, potency, and lack of side effects) are consistent with the goals of the final product. The interferon-containing powder can be blown into the filter end of a premade cigarette, using air blasts of short duration which move a predetermined amount of interferon powder a distance not to substantially exceed the distance to the filter plus the length of filter itself (FIG. 1). Interferon particles become loosely admixed with and imbedded in filters of cellulose acetate, a substance which will not otherwise retain the particles through strong bonds. The process is not limited to cigarettes with filters of cellulose acetate, however, but is directly suitable for any filters which will not chemically attract interferon in a permanent fashion and can be modified by the addition of a cellulose acetate or some other prefilter to include cigarettes containing any other kind of filter. The process can be adapted to filterless cigarettes, cigars, pipes, and other smoking devices by including in the smoke flow of the device a matrix like cellulose, cellulose acetate, etc., admixed with interferon particles. The act of smoking represents reversal of the airflow used to combine the pieces of interferon with the cigarette and will draw particles of interferon into the smoke, carrying interferon to cells exposed to the cigarette smoke.

An exemplary device for combining interferon particles with cigarette filters or prefilters is depicted in FIG. 4. A blast of air is supplied by a conventional air source—compressor, impellor motor, diaphragm, etc. The air is driven along a tube and flows past an interferon-dispensing device, for example, a chamber which is agitated or otherwise handled or constructed to maintain a uniform density of ariborne interferon particles and which dispenses a known volume of its contents into the tube. A piston device is pictured in FIG. 1 but any device is suitable as long as it can deliver suitable quantities of interferon particles to the tube. A predetermined volume of the airborne particles is introduced into the tube just before the blast of air is generated. During the air blast, the interferon particles are carried a determined distance into the cigarette, which was fabricated by conventional processes. The air blast is terminated and the interferon particles settle on the filter material. The tube is then moved to the next cigarette (or the cigarettes are moved) and the process is repeated. The above technique was detailed only the way of example. Other means are possible of combining interferon particles prepared by lyophilization with filters, including the deposition of interferon particles onto filter by gravity, spraying, dusting, or other means of causing particle movement or by electrical attraction, magnetic attraction, or other coating or plating processes. These and other alternative methods are included in our invention. Moreover, interferon particles can be combined with filters at any stage of filter fabrication, providing no subsequent step is used involving heating the core of the filter above 850° C. (the temperature required to destroy the peptide bond). Interferon can be combined with tobacco, instead of with the filter or can be combined with a prefilter which is subsequently attached to the cigarette. Interferon can be deposited as a liquid solution or semisolid or colloid, etc. on filter material, tobacco, or a prefilter with similar results although the efficiency of displacement is much less. All of these modifications and future adaptations from this changing field are considered part of the invention. Basically, the invention satisfies the criteria of immobilization of interferon pieces of interferon on or in smoking devices in such a way as to permit the entrainment in the smoke produced by the smoking devices of interferon molecules, or interferon containing particles or complexes of interferon with other substances which may or may not be particulate, in biologically active form.

It is evident from the above description that pieces of inteferon having biological activity and enhanced stability can be generated, isolated, and included in cigarettes. Thus the subject process provides a novel means for counteracting a potentially harmful effect of cigarette smoking as well as providing a generally protective effect on the human respiratory system against common cold, viruses, etc. The use of a piece of interferon lacking several amino acids is merely illustrative of combining the natural anticancer agent, interferon, with cigarettes. Other modifications of interferon are possible, including adding amino acids, changing existing amino acids and altering the various sugar prosthetic groups by removal, addition, or modification.

In accordance with the subject invention, methods are provided for engineering pieces of interferon with desired properties, potent biological activity, enhanced stability, the ability to be included in a cigarette and be released in smoke. As a result, a potentially harmful effect of smoking can be overcome, and indeed converted to increase the general health of the smoker.

Although the foregoing invention has been described in some detail by way of illustration and example for the purpose of clarity and understanding, it will be obvious that certain changes and modifications may be practiced within the scope of the appended claims.

V. Combination of Interferon/Inducer Activators with Cigarettes

Synthetic chemicals which stimulate the body's own interferon reserves are commonly referred to as interferon inducers or interferon inducer/activators (see review in "Selective Inhibitors of Viral Functions" (edited by W. A. Carter, Chemical Rubber Company, 1973). Such inducers are comprised of chemical diverse classes of compounds including double-stranded RNA (ribonucleic acid), or various small molecular weight chemicals such as polyanions, pyran copolymers, etc. (See also "Interferon", edited by I. Gresser, 1981). The subject invention can be practiced with any of the above diverse groups of chemical and/or biochemical substances provided they are consistently displaced from the cigarette, and continue to demonstrate potency upon deposition in the respiratory spaces and remain free of undesirable side effects.

To demonstrate their effectiveness, two inducers, poly I.C and Ampligen (trademark pending for an inducer consisting of mismatched RNA helices) were deposited in lyophilized form an cigarette filters by sprinkling the powders lightly over the filter end of the cigarette. The exemplary device depicted FIG. 1 can also be used with inducer particles or to prepare any combination of inducer particles and interferon particles. The combination of the two substances, in various tests conducted outside the body, usually resulted in more pronounced, or synergistic, desirable biological effects.

EXAMPLES

BACKGROUND TO EXAMPLES

The human lung and surrounding tissues is a complex organ composed of many different types of cells which respond to assaults of external environmental substances during the necessary process of exchanging gases (oxygen received for carbon dioxide expelled). To evaluate the beneficial results of the invention, we have chosen to study components of the respiratory defense system outside the body through the use of various living human cells maintained outside the body in small tissue culture vessels, petri dishes, or wells. In such dishes, or other devices for human cell growth, smoke can be blown upon the living cells in a way which simulates some of the types of interactions which will occur within the human body.

EXAMPLE 1

A human volunteer inspired from each of a group of filter tipped (cellulose acetate) cigarettes onto which had been previously deposited in lyophilized form the equivalent of 100,000 Internation Reference Units (IRUs) of either natural fibroblast (Beta) interferon (Cigarette A), or 100,000 IRUs natural Beta interferon fragment peptide as described in Section II (Cigarette B) or 10 micrograms of the mismatched RNA interferon inducer (see Carter, et. al., Journal of Molecular Biology, Volume 70 page 567, 1972) (Cigarette C). Promptly upon inspiring the smoke which had passed through the filters impregnated with the lyophilized interferon components, the volunteer discharged through his oral cavity and nose the smoke directly upon an open petri dish containing normal living human fibroblast cells which had been maintained in medium RPMI 1640 supplemented with serum. The petri dishes were then returned to a carbon dioxide (5%) and liquid medium environment for 12 additional hours allowing time for the interferon effect to take place after which the interferon antiviral activity in the fibroblastic cells was determined by a standard assay of inhibition of virus induced cytopathic effect; see Armstrong, J. A., Applied Microbiology, Volume 21 pp. 723-725, 1971. Vesicular stomatitis virus was the challenge virus. In all dishes which had received smoke which passed subsequently through the interferon-impregnated filter and thence through the oral cavity of the volunteer smoker, strong evidence of an antiviral state was observed in the resident fibroblastic cells. In a similar experiment using a "control" cigarette lacking an interferon-treated filter, no antiviral effects were discernible, indicating that cigarettes smoke per se does not afford protection of human tissues against the challenge viruses.

EXAMPLE 2

A volunteer repeated the procedure described above with identically prepared cigarettes, A, B, C, and D consisting of 100,000 IRUs of natural human immune interferon (gamma) prepared as previously described (Mizrahi et. al., ibid, 1978). The gamma interferon contained 100,000 IRUs per milligralm of protein, thereby having an estimated purity of appproximately 1 percent. In this instance, the smoke was discharged directly into wells containing human immune natural killer (NK) cells which had been isolated by standard techniques including the use of Ficoll-Hypaque gradients using cells from the blood of health human subjects (see Zarling, Carter, et. al., Journal of Immunology, Volume 123 pp. 63–70, 1979 and ibid, Volume 124 pp. 1852–1857, 1981). The petri dishes were then reincubated for 8 hours after which the NK cells were reisolated by standard procedures and tested for ability to kill the human tumor target cells K562 (above references; see also Marx, Science, Volume 210 pp. 624–626, 1981). The NK cells were considerably augmented in their killing ability some 30–100 percent as a result from exposure to smoke from cigarettes A, B, C, and D. Smoke from "control" cigarettes demonstrated no augmentation abilities, indicating that the effect was not a non-specific one, but rather resided from the interferon containing components and interferon including substances which had been purposefully added to the cigarettes.

EXAMPLE 3

A volunteer repeated the above experiment now using different target cells and an enlarged panel of treated cigarettes. In this instance, the target cells consisted of human macrophages (as defined by their adherence to the plastic petri dish) derived from cells circulating in the blood of normal individuals (Zarling, ibid; see also Schultz and Chirigos, Cancer Research, Volume 38 pp. 1003–1007, 1978). In this instance, the NK cells, being non-adherent to surfaces, were first discarded and the macrophages which remained could be maintained in a living stage in medium RPMI 1640 supplemented with fetal bovine serum. The enlarged panel of interferon cigarettes consisted of the above (Cigerettes A, B, C, and D) and E which contained 100,000 IRU of lyophilized synthetic (bacterial produced) human leukocyte interferon, designated clone $A_2$ (see also Goeddel, D. V., et. al., Nature, Volume 290 pp. 20–26, 1981). Macrophage activation was measured by the enlargement of iron particles 12 hours after exposure to the smoke. During the interim, cells were maintained in a humidified, 5% $CO_2$ chamber at 37°. As in Examples 1 to 2, all human macrophages preparations exposed to smoke from interferon bearing cigarettes were consistently activated while smoke from "control" cigarettes showed no effect.

EXAMPLE 4

A volunteer repeated experiment 3 (Cigarettes A, B, C, D, and E) using a new target tissue culture wells containing the human tumor HL60 cells. HL60 cells are very malignant leukemic tumor cells as suggested by their primitive cellular architecture; however, on direct exposure to interferon, a percentage of the cells undergo morphological changes indicating maturation and return to normal cell appearance and function (Carter, grant application P01CA29545 and references cited therein). Following exposure to the individual smoke streams, the petri dishes containing HL60 cells were maintained in a humidified 5% $CO_2$ chamber at 37° in medium MEM. Every 48 hours for the next 5 to 10 days, the cells were repeatedly exposed to the interferon—containing smoke, and then reincubated in $CO_2$ chambers. Beginning on about the 7th day after the experiment had begun, and continuing through the 14th day, the interferon treated HL60 cultures (exposed to smoke first drawn through filters of interferon in cigarettes A through E) showed progressive signs of maturation of normal development as compared to the control cultures. Indices of maturation and return to normalcy included: the progressive segmentation of cell nuclei, gradual disappearance of nucleoli and reduction in nuclear size, evidence of cytoplasmic granulations and evidence of differentiation into mature polymorphonuclear leukocyte, such as those typically detected in normal human peripheral blood.

EXAMPLE 5

Interferon, prepared with or without albumin as described in Section III and freeze-dried, was rehydrated in 1 ml of distilled water and then stored at various temperatures in polypropylene containers. At intervals, aliquots were taken and interferon antiviral activity was measured. The results are presented in Table 1 below:

| Human Albumin | Storage Temperature | Activity* after 24 hrs. | Activity* after 1 wk. | Activity* after 1 month | Activity* after 1 year |
|---|---|---|---|---|---|
| + | +22° C. | 99 | 79 | 37 | 0** |
| − |   | 75 | 16 | 0.1 | 0** |
| + | 4° & below | 100 | 100 | 95 | 30 |
| − | + | 97 | 85 | 38 | 0** |
| + | +22° C. | 100 | 100 | 100 | 100 |

*percent of initial activity
**not detectable

Interferon in solution was clearly stabilized by albumin. Dry interferon was stable for over 1 year at room temperature in the presence of albumin.

I therefore claim:

1. A process of medicating a smokable tobacco product comprising exogenously adding interferon or biologically active fragments thereof to said product.
2. The process of claim 1 wherein said interferon is stabilized.
3. The process of claim 2 wherein said stabilization results from attachment of said interferon to a carrier.
4. The process of claim 3 wherein said carrier is serum albumin.
5. The process fo claim 3 wherein said carrier is cytochrome C.
6. The process of claim 1 wherein said product is a cigarette.
7. The process of claim 1 wherein said product is a cigar.
8. The process of claim 1 wherein said product is pipe tobacco.
9. A process of medicating smokable tobacco products comprising adding to said products a substance which induces the production of interferon in the human body.
10. The process of claim 9 wherein said substance is selected from the group consisting of double stranded RNA, pyran copolymers, polyanions, and lymphokines.
11. The process of claim 9 wherein said product is a cigarette.
12. The process of claim 9 wherein said product is a cigar.
13. The process of claim 9 wherein said product is pipe tobacco.
14. A smokable tobacco product containing exogenously applied interferon or biologically active fragments thereof.
15. The product of claim 14 wherein said interferon is stabilized.
16. The product of claim 15 wherein said stabilization results from attachment of said interferon to a carrier.
17. The product of claim 16 wherein said carrier is serum albumin.
18. The product of claim 16 wherein said carrier is cytochrome C.
19. A smokable tobacco product containing an exogenously applied substance which induces the production of interferon in the human body.
20. The product of claim 19 wherein said product is a cigarette.
21. The product of claim 19 wherein said product is a cigar.
22. The product of claim 19 wherein said product is pipe tobacco.
23. The product of claim 19 wherein said substance is selected from the group consisting of double stranded RNA, pyran copolymers, polyanions, and lymphokines.
24. The product of claim 1, wherein said product is cigarette.
25. The product of claim 14, wherein said product is a cigar.
26. The product of claim 14, wherein said product is pipe tobacco.
27. A smokable tobacco product containing exogenously applied interferon stabilized by attachment to a carrier.
28. The product of claim 27, wherein said carrier is serum albumin.
29. The product of claim 27, wherein said carrier is cytochrome C.
30. The product of claim 27, wherein said product is a cigarette.
31. The product of claim 27, wherein said product is a cigar.
32. The product of claim 27, wherein said product is pipe tobacco.

* * * * *